(12) United States Patent
Fujikura et al.

(10) Patent No.: US 7,655,633 B2
(45) Date of Patent: Feb. 2, 2010

(54) NITROGEN-CONTAINING HETEROCYCLIC DERIVATIVES, MEDICINAL COMPOSITIONS CONTAINING THE SAME AND MEDICINAL USE THEREOF

(75) Inventors: Hideki Fujikura, Nagano (JP); Toshihiro Nishimura, Nagano (JP); Kenji Katsuno, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 403 days.

(21) Appl. No.: 10/540,519

(22) PCT Filed: Dec. 19, 2003

(86) PCT No.: PCT/JP03/16310

§ 371 (c)(1),
(2), (4) Date: Jun. 23, 2005

(87) PCT Pub. No.: WO2004/058790

PCT Pub. Date: Jul. 15, 2004

(65) Prior Publication Data

US 2006/0035840 A1     Feb. 16, 2006

(30) Foreign Application Priority Data

Dec. 25, 2002   (JP) .............................. 2002-374016

(51) Int. Cl.
  *A01N 43/04*   (2006.01)
  *A61K 31/70*   (2006.01)
  *C07H 15/24*   (2006.01)

(52) U.S. Cl. .............................. 514/35; 514/25; 514/27; 536/4.1; 536/17.2; 536/17.3; 536/17.4; 536/18.1

(58) Field of Classification Search .................. None
See application file for complete search history.

(56) References Cited

U.S. PATENT DOCUMENTS 7,271,153 B2 * 9/2007 Nishimura et al. ............ 514/27

2002/0111315 A1   8/2002   Washburn et al.
2005/0049203 A1   3/2005   Nishimura et al.

FOREIGN PATENT DOCUMENTS

| EP | 1213296 A1 | 6/2002 |
|---|---|---|
| WO | WO 01/74834 A1 | 10/2001 |
| WO | WO03/000712 | * 1/2003 |
| WO | WO 03/000712 A1 | 1/2003 |

OTHER PUBLICATIONS

Adachi et al., "T-1095, a Renal Na+-Glucose Transport Inhibitor", Metabolism, vol. 49 (8) 2000, 990-995.*

* cited by examiner

*Primary Examiner*—Traviss C McIntosh, III
(74) *Attorney, Agent, or Firm*—Sughrue Mion, PLLC

(57) ABSTRACT

The present invention provides nitrogen-containing heterocyclic derivatives represented by the general formula:

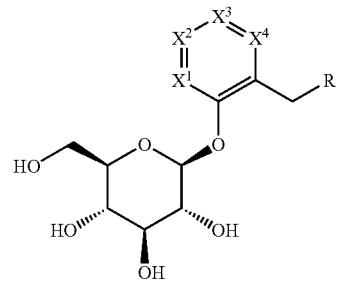

(I)

wherein $X^1$ represents N or $CR^1$; $X^2$ represents N or $CR^2$; $X^3$ represents N or $CR^3$; $X^4$ represents N or $CR^4$; and with the proviso that one or two of $X^1$ to $X^4$ represent N; R represents optionally substituted $C_{3-8}$ cycloalkyl, optionally substituted $C_{6-10}$ aryl, etc.; $R^1$ to $R^4$ represent H, a halogen atom, etc.) or pharmaceutically acceptable salts thereof, or prodrugs thereof, which exert an excellent inhibitory activity in human SGLT2 and are useful as agents for the prevention or treatment of a disease associated with hyperglycemia such as diabetes, diabetic complications, obesity or the like, pharmaceutical compositions comprising the same, and medicinal uses thereof.

21 Claims, No Drawings

NITROGEN-CONTAINING HETEROCYCLIC DERIVATIVES, MEDICINAL COMPOSITIONS CONTAINING THE SAME AND MEDICINAL USE THEREOF

TECHNICAL FIELD

The present invention relates to nitrogen-containing heterocyclic derivatives or pharmaceutically acceptable salts thereof, or prodrugs thereof which are useful as medicaments, pharmaceutical compositions comprising the same and pharmaceutical uses thereof.

More particularly, the present invention relates to nitrogen-containing heterocyclic derivatives or pharmaceutically acceptable salts thereof, or prodrugs thereof which exhibit an inhibitory activity inhuman SGLT2 and are useful as agents for the prevention or treatment of a disease associated with hyperglycemia such as diabetes, diabetic complications, obesity or the like, pharmaceutical compositions comprising the same, and pharmaceutical uses thereof.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas, insulin sensitivity enhancers and the like have been employed as antidiabetic agents. However, biguanides and sulfonylureas show occasionally adverse effects such as lactic acidosis and hypoglycemia, respectively. Insulin sensitivity enhancers show occasionally adverse effects such as edema, and are concerned for advancing obesity. Therefore, in order to solve these problems, it has been desired to develop antidiabetic agents having a new mechanism.

In recent years, research and development of new type antidiabetic agents have been progressing, which promote urinary glucose excretion and lower blood glucose level by preventing reabsorption of excess glucose at the kidney (for example, see the following Reference 1). In addition, it is reported that SGLT2 (Na⁺/glucose cotransporter 2) is present in the S1 segment of the kidney's proximal tubule and participates mainly in reabsorption of glucose filtrated through glomerular (for example, see the following Reference 2). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents which have a potent inhibitory activity in human SGLT2 and have a new mechanism has been desired. In addition, since such agents for promoting the excretion of urinary glucose excrete excess glucose though the urine and consequently the glucose accumulation in the body is decreased, they are also expected to have a preventing or alleviating effect on obesity and a diuretic effect. Furthermore, the agents are considered to be useful for various related diseases which occur accompanying the progress of diabetes or obesity due to hyperglycemia.

Reference 1: Luciano Rossetti, and other 4 persons, J. Clin. Invest., May 1987, Vol. 79, pp. 1510-1515

Reference 2: Yoshikatsu Kanai, and other 4 persons, J. Clin. Invest., January 1994, Vol. 93, pp. 397-404

DISCLOSURE OF THE INVENTION

The present inventors have studied earnestly to find compounds having an inhibitory activity in human SGLT2. As a result, it was found that compounds represented by the following general formula (I) show an excellent inhibitory activity in human SGLT2, thereby forming the basis of the present invention.

The present invention is to provide the following nitrogen-containing heterocyclic derivatives or pharmaceutically acceptable salts thereof or prodrugs thereof which show an excellent hypoglycemic effect by exerting an inhibitory activity in human SGLT2 and excreting excess glucose in the urine through preventing the reabsorption of glucose at the kidney, pharmaceutical compositions comprising the same, and pharmaceutical uses thereof and production intermediates thereof.

This is, the present invention relates to

[1] a nitrogen-containing heterocyclic derivative represented by the general formula:

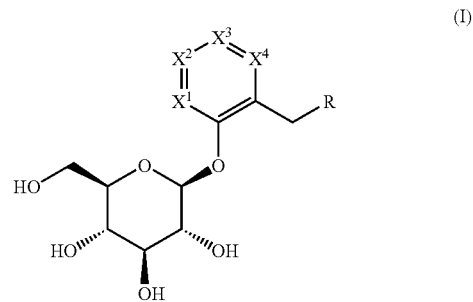

(I)

[wherein
$X^1$ represents N or $CR^1$;
$X^2$ represents N or $CR^2$;
$X^3$ represents N or $CR^3$;
$X^4$ represents N or $CR^4$;

and with the proviso that one or two of $X^1$, $X^2$, $X^3$ and $X^4$ represent N;

R represents a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);

$R^1$ to $R^4$ are the same or different, independently represents a hydrogen atom or a group selected from the following substituent group (D);

substituent group (A) consists of a halogen atom, a nitro group, a cyano group, an oxo group, -$G^1$, —$OG^2$, —$SG^2$, —$N(G^2)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC(=O)N(G^2)_2$, —$NHC(=O)G^2$, —$OS(=O)_2G^1$, —$NHS(=O)_2G^1$ and —$C(=O)NHS(=O)_2G^1$;

substituent group(B) consists of a halogen atom, a nitro group, a cyano group, -$G^1$, —$OG^2$, —$SG^2$, —$N(G^2)_2$, -$G^3OG^4$, -$G^3N(G^4)_2$, —$C(=O)G^2$, —$C(=O)OG^2$, —$C(=O)N(G^2)_2$, —$S(=O)_2G^2$, —$S(=O)_2OG^2$, —$S(=O)_2N(G^2)_2$, —$S(=O)G^1$, —$OC(=O)G^1$, —$OC$ (=O)N(G²)₂, —NHC(=O)G², —OS(=O)₂G¹, —NHS(=O)₂G¹ and —C(=O)NHS(=O)₂G¹

(in the substituent group (A) and/or (B), G¹ represents a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (C), a C₁₋₉ heteroaryl group which may have the same or different 1 to 3 groups selected from the following substituent group (D);

G² represents a hydrogen atom, a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (D), a C₁₋₉ heteroaryl group which may have the same or different 1 to 3 groups selected from the following substituent group (D), and with the proviso that G² are the same or different when there are more than one G² in the substituents;

G³ represents a C₁₋₆ alkyl group;

G⁴ represents a C₁₋₆ alkyl group which may have the same or different 1 to 3 groups selected from the following substituent group (C), and with the proviso that G⁴ are the same or different when there are more than one G⁴ in the substituents;

substituent group (C) consists of a halogen atom, a nitro group, a cyano group, an oxo group, -G⁵, —OG⁶, —SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC(=O)N(G⁶)₂, —NHC(=O)G⁶, —OS(=O)₂G⁵, —NHS(=O)₂G⁵ and —C(=O)NHS(=O)₂G⁵; and substituent group (D) consists of a halogen atom, a nitro group, a cyano group, -G⁵, —OG⁶, —SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC(=O)N(G⁶)₂, —NHC(=O)G⁶, —OS(=O)₂G⁵, —NHS(=O)₂G⁵ and —C(=O)NHS(=O)₂G⁵

(in the substituent group (C) and/or (D), G⁵ represents a C₁₋₆ alkyl group, a HO—C₁₋₆ alkyl group, a C₂₋₆ alkenyl group, a C₂₋₆ alkynyl group, a C₃₋₈ cycloalkyl group, a C₆₋₁₀ aryl group, a C₂₋₉ heterocycloalkyl group or a C₁₋₉ heteroaryl group;

G⁶ represents a hydrogen atom, a C₁₋₆ alkyl group, a C₂₋₆ alkenyl group, a C₂₋₆ alkynyl group, a C₃₋₈ cycloalkyl group, a C₆₋₁₀ aryl group, a C₂₋₉ heterocycloalkyl group or a C₁₋₉ heteroaryl group, and with the proviso that G⁶ are the same or different when there are more than one G⁶ in the substituents))

and with the proviso that when X¹ and X³ independently represent N or CH;

X² represents N or CR² (with the proviso that R² represents a hydrogen atom, a halogen atom, a C₁₋₆alkyl group, a C₃₋₈cycloalkyl group, —O—C₁₋₆ alkyl, an amino group, —NH—C₂₋₇ acyl, —NH—C₁₋₆ alkyl or —N(C₁₋₆ alkyl)₂); and X⁴ represents N or CR⁴ (with the proviso that R⁴ represents a hydrogen atom or a C₁₋₆ alkyl group), R represents the above-defined group except for the following substituent:

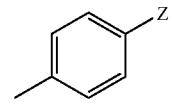

(wherein Z represents a hydrogen atom, a halogen atom, a C₁₋₆ alkyl group which may have a substituent selected from the following substituent group (α), —O—C₁₋₆ alkyl which may have a substituent selected from the following substituent group (β), —S—C₁₋₆ alkyl which may have a substituent selected from the following substituent group (β) or a C₃₋₈ cycloalkyl group; substituent group (α) consists of a halogen atom, a hydroxy group and —O—C₁₋₆ alkyl; and substituent group (β) consists of a hydroxy group and —O—C₁₋₆ alkyl)] or a pharmaceutically acceptable salt thereof, or a prodrug thereof;

[2] a nitrogen-containing heterocyclic derivative as described in the above [1] wherein R represents a phenyl group which may have the same or different 1 to 3 groups selected from the following substituent group (B), or a pharmaceutically acceptable salt thereof, or a prodrug thereof [wherein substituent group (B) consists of a halogen atom, a nitro group, a cyano group, -G¹, —OG², —SG², —N(G²)₂, -G³OG⁴, -G³N(G⁴)₂, —C(=O)G², —C(=O)OG², —C(=O)N(G²)₂, —S(=O)₂G², —S(=O)₂OG², —S(=O)₂N(G²)₂, —S(=O)G¹, —OC(=O)G¹, —OC(=O)N(G²)₂, —NHC(=O)G², —OS(=O)₂G¹, —NHS(=O)₂G¹ and —C(=O)NHS(=O)₂G¹ (in the substituent group (B), G¹ represents a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (C), a C₁₋₉ heteroaryl group which may have the same or different 1 to 3 groups selected from the following substituent group (D);

G² represents a hydrogen atom, a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a $C_{2-9}$ heterocycloalkyl group which may have the same or different 1 to 3 groups selected from the following substituent group (D), a $C_{1-9}$ heteroaryl group which may have the same or different 1 to 3 groups selected from the following substituent group (D), and with the proviso that $G^2$ are the same or different when there are more than one $G^2$ in the substituents; $G^3$ represents a $C_{1-6}$ alkyl group;

$G^4$ represents a $C_{1-6}$ alkyl group which may have the same or different 1 to 3 groups selected from the following substituent group (C), and with the proviso that $G^4$ are the same or different when there are more than one $G^4$ in the substituents;

substituent group (C) consists of a halogen atom, a nitro group, a cyano group, an oxo group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$; and substituent group (D) consists of a halogen atom, a nitro group, a cyano group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$ (in the substituent group (C) and/or (D), $G^5$ represents a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{2-9}$ heterocycloalkyl group or a $C_{1-9}$ heteroaryl group and with the proviso that $G^6$ are the same or different when there are more than one $G^6$ in the substituents))];

[3] a pharmaceutical composition comprising as an active ingredient a nitrogen-containing heterocyclic derivative as described in the above [1] or [2], or a pharmaceutically acceptable salt thereof, or a prodrug thereof;

[4] a pharmaceutical composition as described in the above [3] wherein the composition is a human SGLT2 inhibitor;

[5] a pharmaceutical composition as described in the above [4] wherein the composition is an agent for the prevention or treatment of a disease associated with hyperglycemia;

[6] a pharmaceutical composition as described in the above [5] wherein the disease associated with hyperglycemia is selected from the group consisting of diabetes, diabetic complications, obesity, hyperinsulinemia, glucose metabolism disorders, hyperlipidemia, hypercholesterolemia, hypertriglyceridemia, lipid metabolism disorders, atherosclerosis, hypertension, congestive heart failure, edema, hyperuricemia and gout;

[7] a pharmaceutical composition as described in the above [6] wherein the disease associated with hyperglycemia is diabetes;

[8] a pharmaceutical composition as described in the above [6] wherein the disease associated with hyperglycemia is diabetic complications;

[9] a pharmaceutical composition as described in the above [6] wherein the disease associated with hyperglycemia is obesity;

[10] a method for the prevention or treatment of a disease associated with hyperglycemia, which comprises administering an effective amount of a nitrogen-containing heterocyclic derivative as described in the above [1] or [2], or a pharmaceutically acceptable salt thereof, or a prodrug thereof;

[11] a use of a nitrogen-containing heterocyclic derivative as described in the above [1] or [2], or a pharmaceutically acceptable salt thereof, or a prodrug thereof for the manufacture of a pharmaceutical composition for the prevention or treatment of a disease associated with hyperglycemia;

[12] a pharmaceutical combination which comprises (A) a nitrogen-containing heterocyclic derivative as described in the above [1] or [2], or a pharmaceutically acceptable salt thereof, or a prodrug thereof, and (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[13] a pharmaceutical combination as described in the above [12] for the prevention or treatment of a disease associated with hyperglycemia;

[14] a pharmaceutical combination as described in the above [13] wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant, and the disease associated with hyperglycemia is diabetes;

[15] a pharmaceutical combination as described in the above [14] wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist;

[16] a pharmaceutical combination as described in the above [15] wherein a component (B) is at least one member selected from the group consisting of an insulin sensitivity enhancer, a glucose absorption inhibitor, a biguanide, an insulin secretion enhancer and insulin or an insulin analogue;

[17] a pharmaceutical combination as described in the above [13] wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endo-peptidase inhibitor, an angiotensin II receptor antagonist, an endothelin-converting enzyme inhibitor, an endothelin receptor antagonist and a diuretic agent, and the disease associated with hyperglycemia is diabetic complications;

[18] a pharmaceutical combination as described in the above [17] wherein a component (B) is at least one member selected from the group consisting of an aldose reductase inhibitor, an angiotensin-converting enzyme inhibitor, a neutral endopeptidase inhibitor and an angiotensin II receptor antagonist;

[19] a pharmaceutical combination as described in the above [13] wherein a component (B) is at least one member selected from the group consisting of an insulin sensitivity enhancer, a glucose absorption inhibitor, a biguanide, an insulin secretion enhancer, an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant, and the disease associated with hyperglycemia is obesity;

[20] a pharmaceutical combination as described in the above [19] wherein a component (B) is at least one member selected from the group consisting of a $\beta_3$-adrenoceptor agonist and an appetite suppressant;

[21] a pharmaceutical combination as described in the above [20] wherein the appetite suppressant is a drug selected from the group consisting of a monoamine reuptake inhibitor, a serotonin reuptake inhibitor, a serotonin releasing stimulant, a serotonin agonist, a noradrenaline reuptake inhibitor, a noradrenaline releasing stimulant, an $\alpha_1$-adrenoceptor agonist, a $\beta_2$-adrenoceptor agonist, a dopamine agonist, a cannabinoid receptor antagonist, a γ-aminobutyric acid receptor antagonist, a $H_3$-histamine antagonist, L-histidine, leptin, a leptin analogue, a leptin receptor agonist, a melanocortin receptor agonist, α-melanocyte stimulating hormone, cocaine-and amphetamine-regulated transcript, mahogany protein, an enterostatin agonist, calcitonin, calcitonin-gene-related peptide, bombesin, a cholecystokinin agonist, corticotropin-releasing hormone, a corticotropin-releasing hormone analogue, a corticotropin-releasing hormone agonist, urocortin, somatostatin, a somatostatin analogue, a somatostatin receptor agonist, pituitary adenylate cyclase-activating peptide, brain-derived neurotrophic factor, ciliary neurotrophic factor, thyrotropin-releasing hormone, neurotensin, sauvagine, a neuropeptide Y antagonist, an opioid peptide antagonist, a galanin antagonist, a melanin-concentrating hormone receptor antagonist, an agouti-related protein inhibitor and an orexin receptor antagonist;

[22] a method for the prevention or treatment of a disease associated with hyperglycemia, which comprises administering an effective amount of (A) a nitrogen-containing heterocyclic derivative as described in the above [1] or [2], or a pharmaceutically acceptable salt thereof, or a prodrug thereof, in combination with (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer;

[23] a use of (A) a nitrogen-containing heterocyclic derivative as described in the above [1] or [2], or a pharmaceutically acceptable salt thereof, or a prodrug thereof, and (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia; and the like.

In the present invention, the term "$C_{1-6}$ alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "$C_{2-6}$ alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group or the like; and the term "$C_{2-6}$ alkynyl group" means a straight-chained or branched alkynyl group having 2 to 6 carbon atoms such as an ethynyl group, a 2-propinyl group or the like. The term "$C_{2-7}$ acyl group" means a straight-chained or branched acyl group having 2 to 7 carbon atoms such as an acetyl group, a propionyl group, a butyryl group, an isobutyryl group, a valeryl group, a pivaloyl group, a hexanoyl group or the like; the term "$C_{3-8}$ cycloalkyl group" means a cyclopropyl group, a cyclobutyl group, a cyclopentyl group, a cyclohexyl group, a cycloheptyl group or a cyclooctyl group; and the term "$C_{6-10}$ aryl group" means a phenyl group or a naphthyl group. The term "$C_{2-9}$ heterocycloalkyl group" means a group derived from a 3 to 8-membered heterocycloalkyl group containing the same or different 1 or 2 hetero atoms selected from an oxygen atom, a sulfur atom and a nitrogen atom in the ring such as morpholine, thiomorpholine, tetrahydrofuran, tetrahydropyran, aziridine, azetidine, pyrrolidine, imidazolidine, oxazoline, piperidine, piperazine, pyrazolidine or the like, or a group derived from a 5 or 6-membered heterocycloalkyl group as defined above fused with an aliphatic or aromatic carbocycle or a heterocycle such as a cyclohexane ring, a benzene ring, a pyridine ring or the like. The term "$C_{1-9}$ heteroaryl group" means a group derived from a 5 or 6-membered heteroaryl group containing the same or different 1 to 4 hetero atoms selected from an oxygen atom, a sulfur atom and a nitrogen atom in the ring such as thiazole, oxazole, isothiazole, isoxazole, pyridine, pyrimidine, pyrazine, pyridazine, pyrrole, thiophene, imidazole, pyrazole, oxadiazole, thiadiazole, tetrazole, furazan or the like, or a group derived from the above heteroaryl group fused with a 5 or 6-membered aromatic carbocycle or heterocycle such as a benzene ring, a pyrazole ring, a pyridine ring or the like. The term "halogen atom" means a fluorine atom, a chlorine atom, a bromine atom or an iodine atom.

In the present invention, the term "prodrug" means a compound which is converted into a nitrogen-containing heterocyclic derivative represented by the above general formula (I) as an active form thereof in vivo. As prodrugs of a nitrogen-containing heterocyclic derivative represented by the above general formula (I) or pharmaceutically acceptable salts, for example, a compound represented by the general formula:

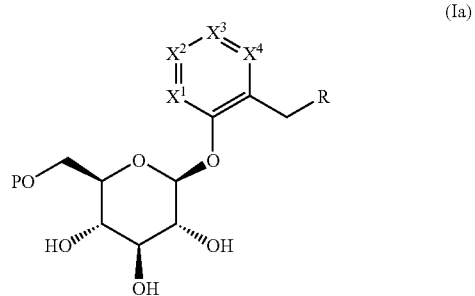

(Ia)

wherein P represents a group forming a prodrug; and $X^1$, $X^2$, $X^3$, $X^4$ and R have the same meanings as defined above, or a pharmaceutically acceptable salt thereof are illustrated.

As examples of groups forming prodrugs, a hydroxy-protective group which can be used generally in a prodrug such as a $C_{2-20}$ acyl group, a $C_{1-6}$ alkyl-O—$C_{2-7}$ acyl group, a $C_{1-6}$ alkyl-OC(=O)—C$_{2-7}$ acyl group, C$_{1-6}$ alkyl-OC(=O)—, C$_{1-6}$ alkyl-O—C$_{1-6}$alkyl-OC(=O)—, a benzoyl group, a C$_{2-7}$acyl-O-methyl group, a 1-(C$_{2-7}$acyl-O-) ethyl group, a C$_{1-6}$alkyl-OC(=O)O-methyl group, a 1-(C$_{1-6}$ alkyl-OC(=O)O-)ethyl group, a C$_{3-8}$ cycloalkyl-OC(=O)O-methyl group, a 1-(C$_{3-8}$ cycloalkyl-OC(=O)O-)ethyl group, an ester group condensed with an amino acid, a phosphoric acid derivative or a cinnamic acid derivative and the like can be illustrated, and an amino-protective group which can be used generally in a prodrug such as a C$_{2-7}$ acyl group, a C$_{1-6}$ alkyl-O—C$_{2-7}$ acyl group, a C$_{1-6}$ alkyl-OC(=O)—C$_{2-7}$ acyl group, C$_{1-6}$ alkyl-OC(=O)—, C$_{1-6}$ alkyl-O—C$_{1-6}$alkyl-OC(=O)—, a benzoyl group, a C$_{2-7}$acyl-O-methyl group, a 1-(C$_{2-7}$acyl-O-)ethyl group, a C$_{1-6}$alkyl-OC(=O)O-methyl group, a 1-(C$_{1-6}$ alkyl-OC(=O)O-)ethyl group, a C$_{3-8}$ cycloalkyl-OC(=O)O-methyl group, a 1-(C$_{3-8}$ cycloalkyl-OC(=O)O-)ethyl group, an amide group condensed with an amino acid and the like can be illustrated. Moreover, a sulfonamide-protective group which can be used generally in a prodrug such as a C$_{2-7}$ acyl-O-methyl group, a 1-(C$_{2-7}$ acyl-O-)ethyl group, a C$_{1-6}$alkyl-OC(=O)O-methyl group, a 1-(C$_{1-6}$ alkyl-OC(=O)O-)ethyl group, a C$_{3-8}$ cycloalkyl-OC(=O)O-methyl group, a 1-(C$_{3-8}$ cycloalkyl-OC(=O)O-) ethyl group and the like can be illustrated. Furthermore, as examples of groups forming prodrugs, a sugar residue such as a glucopyranosyl group, a galactopyranosyl group and the like can be illustrated, for example, such a group can be introduced into the hydroxy group at the 4 or 6-position of the glucopyranosyl group. Of the compounds of the present invention, in a prodrug, a group forming a prodrug may be at any hydroxy group, amino group, sulfonamide group or the like, and two or more such groups are acceptable. The term "C$_{2-20}$ acyl group" means a straight-chained or branched acyl group having 2 to 20 carbon atoms such as an acetyl group, a propionyl group, a butyryl group, an isobutyryl group, a valeryl group, a pivaloyl group, a hexanoyl group, a lauroyl group, a myristoyl group, a palmitoyl group, a stearoyl group or the like.

The term "hydroxy-protective group" means a hydroxy-protective group used in general organic syntheses such as a benzyl group, a p-methoxybenzyl group, a p-nitrobenzyl group, a methoxymethyl group, a methyl group, an acetyl group, a tert-butyldimethylsilyl group, an allyl group, a benzoyl group, a pivaloyl group, a benzyloxycarbonyl group, a 2-trimethylsilylethoxymethyl group or the like; the term "thiol-protective group" means a thiol-protective group used in general organic syntheses such as a benzyl group, a p-methoxybenzyl group, a p-nitrobenzyl group, an acetyl group, a benzoyl group, a pivaloyl group, a benzyloxycarbonyl group or the like; the term "amino-protective group" means an amino-protective group used in general organic syntheses such as a benzyloxycarbonyl group, a tert-butoxycarbonyl group, a benzyl group, a p-methoxybenzyl group, a trifluoroacetyl group, an acetyl group or the like; and the term "carboxy-protective group" means a carboxy-protective group used in general organic syntheses such as a benzyl group, a tert-butyldimethylsilyl group, an allyl group or the like.

As examples of nitrogen-containing heterocyclic derivatives represented by the above general formula (I) of the present invention, various pyridine derivatives, various pyridazine derivatives, various pyrimidine derivatives, various pyrazine derivatives, various triazine derivatives and various tetrazine derivatives can be illustrated. In addition, in cases that there are tautomers in the present compounds, the present invention includes all tautomers.

The nitrogen-containing heterocyclic derivatives represented by the above general formula (I) of the present invention and prodrugs thereof can be prepared, for example, according to the reactions described by the following Scheme 1.

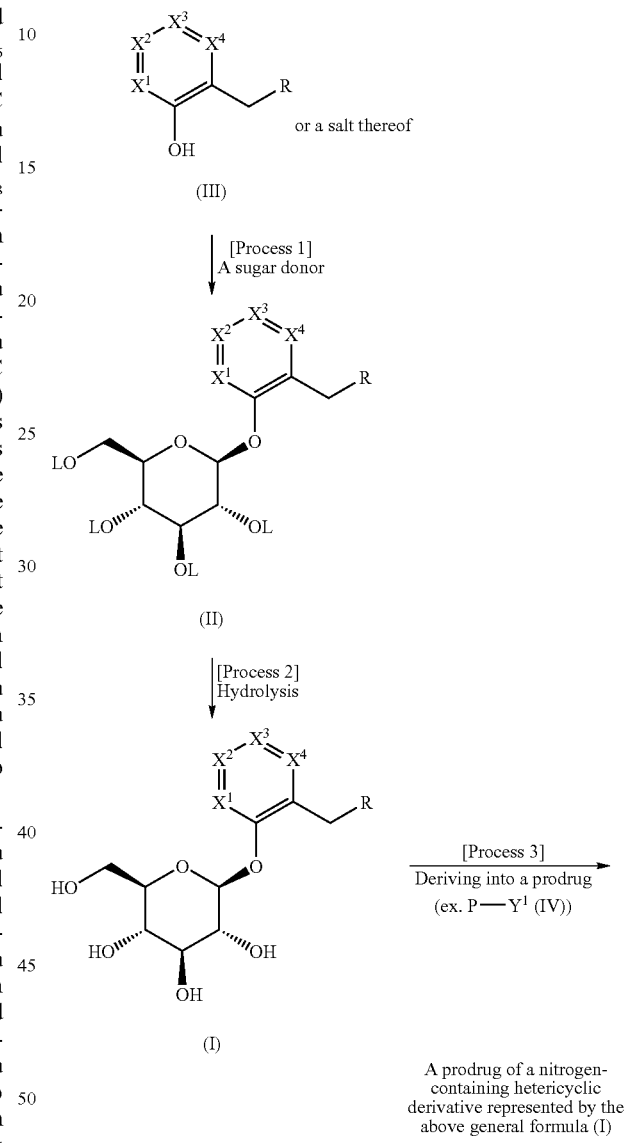

wherein L represents a hydroxy-protective group; P represents a group forming a prodrug; Y$^1$ represents a leaving group such as a chlorine atom, a bromine atom or the like; and X$^1$, X$^2$, X$^3$, X$^4$ and R have the same meanings as defined above.

Process 1

A corresponding compound represented by the above general formula (II) can be prepared by subjecting an alcohol compound represented by the above formula (III) or a salt thereof to glycosidation using a sugar donor such as acetobromo-α-D-glucose in the presence of a silver salt such as silver carbonate, silver oxide or the like or a base such as potassium carbonate, sodium hydride or the like in an inert solvent. As the solvent used in the glycosidation reaction, for example, acetonitrile, tetrahydrofuran, dichloromethane, toluene, N,N-dimethyl-formamide, a mixed solvent and the like can be illustrated. The reaction temperature is usually from room temperature to reflux temperature, and the reaction time is usually from 2 hours to 2 days, varying based on a used starting material, solvent and reaction temperature.

Process 2

A nitrogen-containing heterocyclic derivative represented by the above general formula (I) of the present invention can be prepared by subjecting a compound represented by the above general formula (II) to alkaline hydrolysis. As the solvent used in the alkaline hydrolysis, methanol, ethanol, tetrahydrofuran, water, a mixed solvent thereof and the like can be illustrated, and as the base used, sodium hydroxide, potassium hydroxide, sodium methoxide, sodium ethoxide and the like can be illustrated. The reaction temperature is usually from 0° C. to room temperature, and the reaction time is usually from 30 minutes to 6 hours, varying based on a used starting material, solvent and reaction temperature.

Process 3

A prodrug of a nitrogen-containing heterocyclic derivative represented by the above general formula (I) (for example, a prodrug represented by the above general formula (Ia)) can be prepared by introducing hydroxy-protective groups generally capable for use in a prodrug into hydroxy groups of a nitrogen-containing heterocyclic derivative represented by the above general formula (I) using, for example, an agent for introducing a hydroxy-protective group represented by the above general formula (IV) in the usual way.

For example, a compound represented by the above general formula (III) used as a starting material in the above production method (Scheme 1) can be prepared according to the reactions as described in the following Scheme 2.

Process 4

A compound represented by the above general formula (VI) can be prepared by subjecting a compound represented by the above general formula (V) to oxidation using a Dess-Martin reagent in an inert solvent. As the solvent used in the oxidation, for example, dichloromethane, chloroform, a mixed solvent thereof or the like can be illustrated. The reaction temperature is usually from 0° C. to reflux temperature, and the reaction time is usually from 10 minutes to 1 day, varying based on a used starting material, solvent and reaction temperature.

Process 5

A compound represented by the above general formula (III) can be prepared by subjecting a compound represented by the above general formula (VI) to 1) hydrogenation in the presence or absence of an acid such as hydrochloric acid using a palladium catalyst such as palladium-carbon powder or the like in an inert solvent under a hydrogen atmosphere, or to 2) reduction using a reducing agent. As the solvent used in the 1) hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature. The 2) reduction using a reducing agent can be performed in the presence of a Lewis acid such as trifluoroborate or the like using a reducing agent such as sodium cyanoborohydride or the like in an inert solvent such as tetrahydrofuran. The reaction temperature is usually from room temperature to reflux temperature, and the reaction time is usually from 1 hour to 1 day, varying based on a used starting material, solvent and reaction temperature.

A compound represented by the above general formula (III) used as a starting material in the above production method (Scheme 1) can be also prepared, for example, according to the reactions as described in the following Scheme 3.

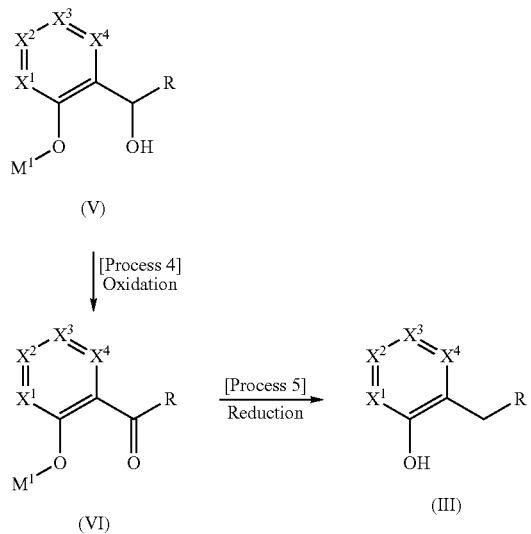

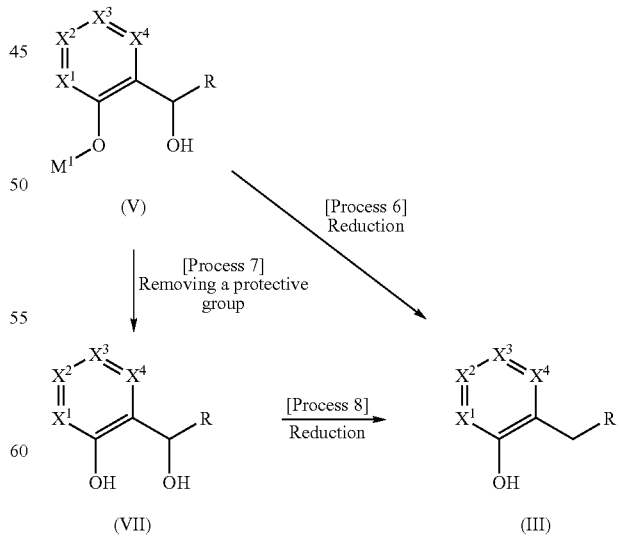

wherein $M^1$ represents a hydroxy-protective group; $M^2$ represents a hydrogen atom or a hydroxy-protective group; and $X^1$, $X^2$, $X^3$, $X^4$ and R have the same meanings as defined above.

wherein $M^1$, $X^1$, $X^2$, $X^3$, $X^4$ and R have the same meanings as defined above.

Process 6

A compound represented by the above general formula (III) can be prepared by subjecting a compound represented by the above general formula (V) to hydrogenation in the presence or absence of an acid such as hydrochloric acid using a palladium catalyst such as palladium-carbon powder in an inert solvent under a hydrogen atmosphere. As the solvent used in the hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 7

A compound represented by the above general formula (VII) can be prepared by removing the protective group $M^1$ of a compound represented by the above general formula (V) in the usual way.

Process 8

A compound represented by the above general formula (III) can be prepared by subjecting a compound represented by the above general formula (VII) to hydrogenation in the presence or absence of an acid such as hydrochloric acid using a palladium catalyst such as palladium-carbon powder in an inert solvent under a hydrogen atmosphere. As the solvent used in the hydrogenation, for example, methanol, ethanol, tetrahydrofuran, ethyl acetate, acetic acid, isopropanol, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Of compounds represented by the above general formula (III) used as starting materials in the above production method (Scheme 1), a compound represented by the following general formula (IIIa) can be prepared, for example, according to the reactions as described in the following Scheme 4.

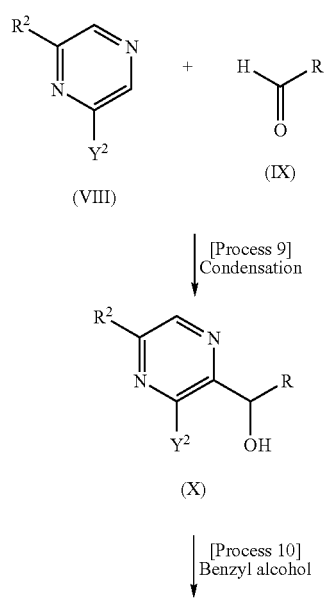

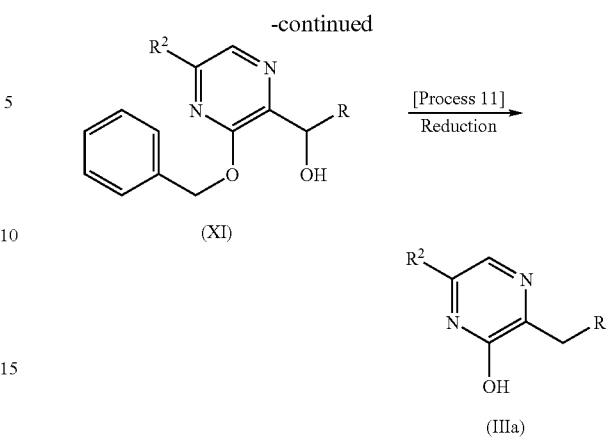

wherein $Y^2$ represents a chlorine atom or a bromine atom; and $R^2$ and R have the same meanings as defined above.

Process 9

A compound represented by the above general formula (X) can be obtained by dissolving a compound represented by the above general formula (VIII) in an inert solvent, allowing the compound to react with lithium 2,2,6,6-tetramethylpiperidide usually at −100° C. to −50° C. and usually for 10 minutes to 2 hours, and allowing the resulting compound to react with a compound represented by the above general formula (IX) usually at −100° C. to room temperature. As the inert solvent used, tetrahydrofuran, diethyl ether, 1,2-dimethoxyethane, a mixed solvent thereof or the like can be illustrated. The reaction time of the condensation reaction is usually from 30 minutes to 6 hours, varying based on a used starting material, solvent and reaction temperature.

Process 10

A compound represented by the above general formula (XI) can be prepared by allowing a compound represented by the above general formula (X) to react with benzyl alcohol in the presence of tris[2-(2-methoxyethoxy)ethyl]amine using a base such as potassium hydroxide, sodium hydroxide, potassium carbonate, sodium carbonate, sodium hydrogen carbonate or the like, in a solvent such as toluene, benzene or the like. The reaction temperature is usually from room temperature to reflux temperature, and the reaction time is usually from 1 hour to 1 day, varying based on a used starting material, solvent and reaction temperature Process 11

A compound represented by the above general formula (IIIa) can be prepared by subjecting a compound represented by the above general formula (XI) to hydrogenation in the presence or absence of an acid such as hydrochloric acid using a palladium catalyst such as palladium-carbon powder in an inert solvent under a hydrogen atmosphere. As the solvent used in the hydrogenation, for example, methanol, ethanol, tetrahydrofuran, ethyl acetate, acetic acid, isopropanol, a mixed solvent thereof or the like can be illustrated. The reaction temperature is usually from room temperature to reflux temperature, and the reaction time is usually from 1 hour to 1 day, varying based on a used starting material, solvent and reaction temperature.

Of compounds represented by the above general formula (III) used as starting materials in the above production method (Scheme 1), a compound represented by the following general formula (IIIb) can be also prepared, for example, according to the reactions as described in the following Scheme 5.

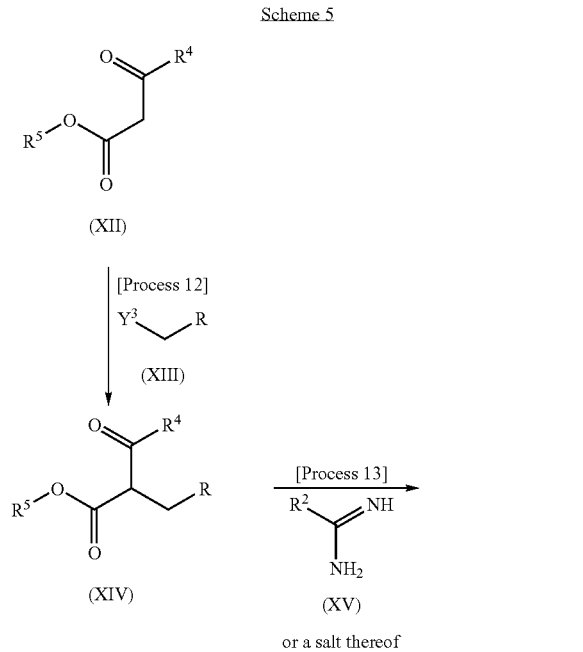

wherein $R^5$ represents a lower alkyl group; $Y^3$ represents a leaving group such as a halogen atom, a mesyloxy group, a tosyloxy group or the like; and $R^2$, $R^4$ and R have the same meanings as defined above.

Process 12

A compound represented by the above general formula (XIV) can be prepared by subjecting a compound represented by the above general formula (XII) to 1) condensation with a benzyl derivative represented by the above general formula (XIII) in the presence of a base such as sodium hydride, potassium tert-butoxide or the like in a solvent such as 1,2-dimethoxyethane, tetrahydrofuran, N,N-dimethylformamide, N,N-dimethyl-acetamide or the like, or to 2) condensation with a benzyl derivative represented by the above general formula (XIII) in the presence or absence of lithium bromide or lithium chloride using a base such as diisopropylethylamine, triethylamine, 1,8-diazabicyclo-[5,4,0]-7-undecene or the like in a solvent such as tetrahydrofuran, diethyl ether, N,N-dimethylformamide, N,N-dimethylacetamide or the like. At the reaction 1), the reaction temperature is usually from room temperature to reflux temperature, and the reaction time is usually from 1 hour to 1 day, varying based on a used starting material, solvent and reaction temperature. In addition, at the reaction 2), the reaction temperature is usually from room temperature to reflux temperature, and the reaction time is usually from 1 hour to 1 day, varying based on a used starting material, solvent and reaction temperature.

Process 13

A compound represented by the above general formula (IIIb) can be obtained by allowing a compound represented by the above general formula (XIV) to react with a compound represented by the above general formula (XV) or a salt thereof in the presence or absence of a base such as sodium methoxide, sodium ethoxide or the like in an alcoholic solvent. As the alcoholic solvent used in the reaction, for example, methanol, ethanol, propanol, a mixed solvent thereof or the like can be illustrated. The reaction temperature is usually from room temperature to reflux temperature, and the reaction time is usually from 2 hours to 2 days, varying based on a used starting material, solvent and reaction temperature.

Of compounds represented by the above general formula (III) used as starting materials in the above production method (Scheme 1), a compound represented by the following general formula (IIIc) can be also prepared, for example, according to the reactions as described in the following Scheme 6.

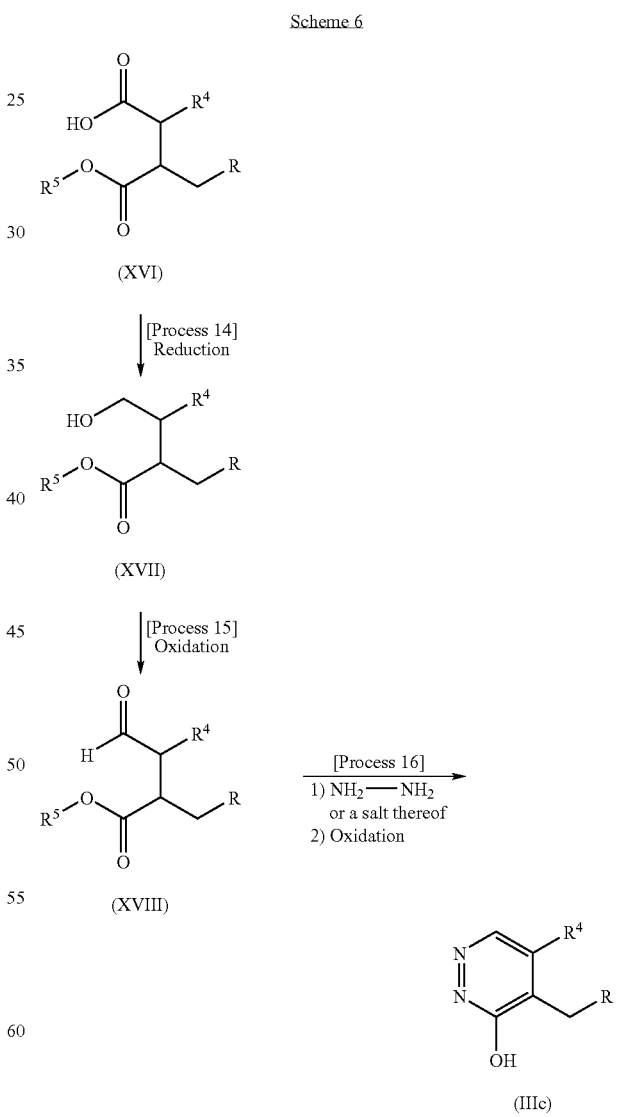

wherein $R^4$, $R^5$ and R have the same meanings as defined above.

Process 14

A compound represented by the above general formula (XVII) can be obtained by reducing a compound represented by the above general formula (XVI) using a reducing agent such as borane-tetrahydrofuran complex, borane-dimethyl-sulfide complex or the like in an inert solvent. As the inert solvent used in the reduction, tetrahydrofuran, diethyl ether, a mixed solvent thereof or the like can be illustrated. The reaction temperature is usually from 0° C. to reflux temperature, and the reaction time is usually from 1 hour to 1 day, varying based on a used starting material, solvent and reaction temperature. In addition, a starting material represented by the above general formula (XVI) can be commercially available or prepared by reaction according to a manner as described in literature or an analogous method thereof, for example, J. Org. Chem., Vol. 37, pp. 555-559 (1972), SYNLETT, pp. 137-138 (1993)

Process 15

A compound represented by the above general formula (XVIII) can be prepared by subjecting a compound represented by the above general formula (XVII) to oxidation using a Dess-Martin reagent in an inert solvent. As the solvent used in the oxidation, for example, dichloromethane, chloroform, a mixed solvent thereof or the like can be illustrated. The reaction temperature is usually from 0° C. to reflux temperature, and the reaction time is usually from 30 minutes to 1 day, varying based on a used starting material, solvent and reaction temperature.

Process 16

A compound represented by the above general formula (IIIc) can be obtained by subjecting a compound represented by the above general formula (XVIII) to cyclization by reaction with hydrazine or a hydrate thereof or a salt thereof in a solvent such as methanol, ethanol, toluene, benzene or a mixed solvent thereof, and then to oxidation using selenium dioxide or the like in an alcoholic solvent such as methanol, ethanol or the like. At the cyclization reaction, the reaction temperature is usually from room temperature to reflux temperature, and the reaction time is usually from 30 minutes to 1 day, varying based on a used starting material, solvent and reaction temperature. At the oxidation reaction, the reaction temperature is usually from room temperature to reflux temperature, and the reaction time is usually from 30 minutes to 2 days, varying based on a used starting material, solvent and reaction temperature.

A compound represented by the above general formula (V) used as a starting material in the above production method (Scheme 2) can be prepared, for example, according to the reactions as described in the following Scheme 7.

Scheme 7

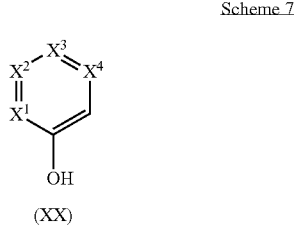

(XX)

[Process 17]
Introducing a protective group

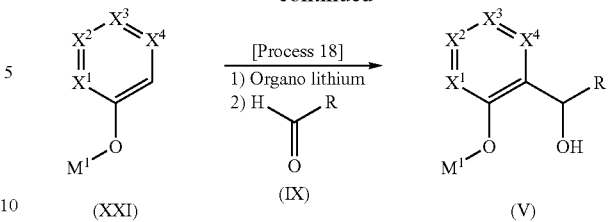

wherein $X^1$, $X^2$, $X^3$, $X^4$, R and $M^1$ have the same meanings as defined above.

Process 17

A compound represented by the above general formula (XXI) can be obtained by introducing a protective group $M^1$ into the hydroxy group of a compound represented by the above general formula (XX) in the usual way.

Process 18

A compound represented by the above general formula (V) can be prepared by dissolving a compound represented by the above general formula (XXI) in an inert solvent, allowing the compound to react with an organo lithium such as tert-butyllithium, n-butyllithium or the like usually at −100° C. to 0° C. usually for 10 minutes to 2 hours, and then allowing the resulting compound to react with a compound represented by the above general formula (IX) added to the reaction mixture, at −100° C. to room temperature. As the inert solvent used in the present reaction, tetrahydrofuran, diethyl ether, 1,2-dimethoxyethane, a mixed solvent thereof or the like can be illustrated. The reaction time at the condensation reaction is usually from 30 minutes to 6 hours, varying based on a used starting material, solvent and reaction temperature.

A compound represented by the above general formula (V) used as a starting material in the above production method (Scheme 2) can be also prepared, for example, according to the reaction as described in the following Scheme 8.

Scheme 8

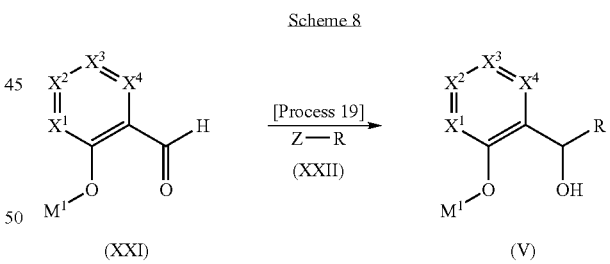

wherein Z represents MgBr, MgCl, MgI or a lithium atom; $X^1$, $X^2$, $X^3$, $X^4$, R and $M^1$ have the same meanings as defined above.

Process 19

A compound represented by the above general formula (V) can be obtained by subjecting a compound represented by the above general formula (XXI) to condensation with a compound represented by the above general formula (XXII) in an inert solvent. As the solvent used in the condensation reaction, for example, tetrahydrofuran, diethyl ether, 1,2-dimethoxyethane, a mixed solvent thereof or the like can be illustrated. The reaction temperature is usually from −100° C. to room temperature, and the reaction time is usually from 30 minutes to 6 hours, varying based on a used starting material, solvent and reaction temperature.

A compound represented by the above general formula (XXI) used as a starting material in the above production method (Scheme 8) can be prepared, for example, according to the reactions as described in the following Scheme 9.

Process 21

A compound represented by the above general formula (XXIII) can be prepared by introducing a protective group $M^1$ into the hydroxy group of a compound represented by the above general formula (XXII) in the usual way.

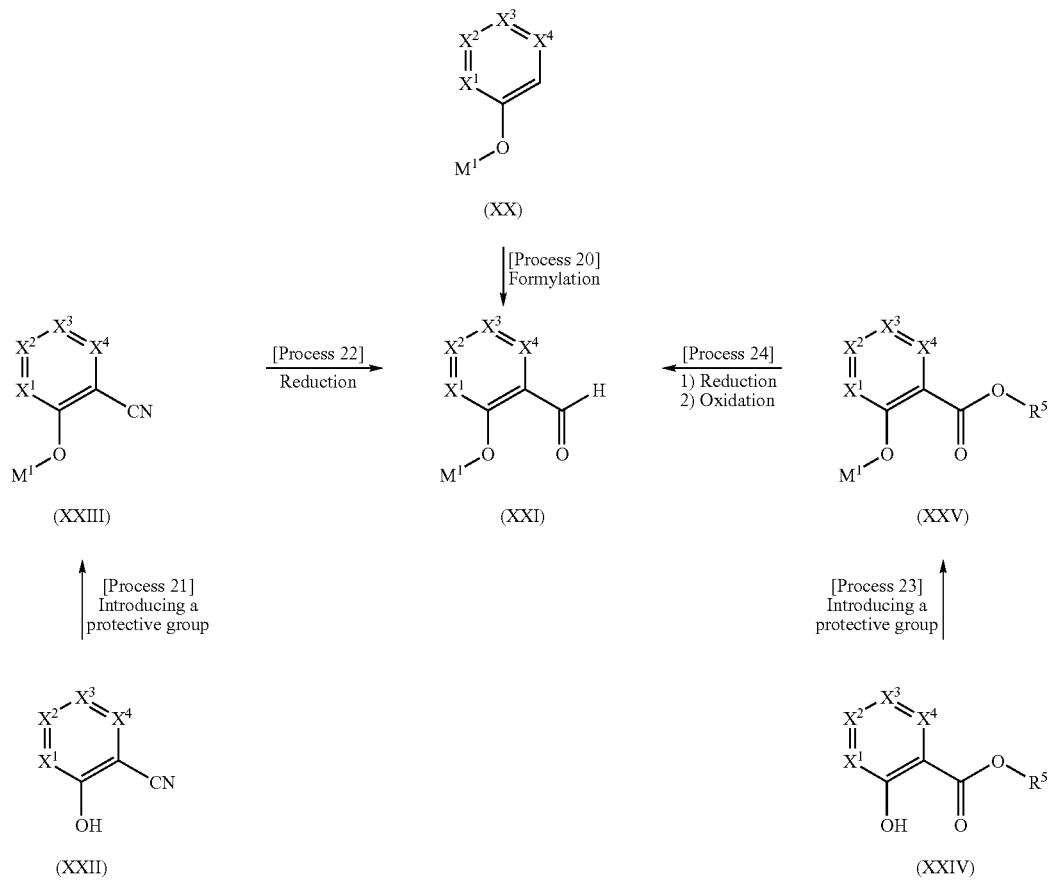

wherein $X^1$, $X^2$, $X^3$, $X^4$, $R^5$ and $M^1$ have the same meanings as defined above.

Process 20

A compound represented by the above general formula (XXI) can be obtained by dissolving a compound represented by the above general formula (XX) in an inert solvent, allowing the compound to react with an organo lithium such as tert-butyllithium, n-butyllithium or the like usually at −100° C. to 0° C. usually for 10 minutes to 2 hours, then adding N,N-dimethylformamide, allowing the mixture to react usually at −100° C. to room temperature usually for 30 minutes to 1 day, and treating the reaction mixture with an aqueous acidic solution. As the inert solvent used, for example, tetrahydrofuran, diethyl ether, 1,2-dimethoxyethane, a mixed solvent thereof or the like can be illustrated, and as an aqueous acidic solution, for example, an aqueous solution of acetic acid, hydrochloric acid, succinic acid, oxalic acid or the like can be illustrated. The treatment time in the aqueous acidic solution is usually from 5 minutes to 30 minutes, varying based on a used aqueous acidic solution and reaction temperature.

Process 22

A compound represented by the above general formula (XXI) can be obtained by subjecting a compound represented by the above general formula (XXIII) using a reducing agent such as diisobutylaluminum hydride or the like in an inert solvent. As the solvent used in the reaction, for example, tetrahydrofuran, dichloromethane, a mixed solvent thereof or the like can be illustrated. The reaction temperature is usually from −100° C. to room temperature, and the reaction time is usually from 1 hour to 6 days, varying based on a used starting material, solvent and reaction temperature.

Process 23

A compound represented by the above general formula (XXV) can be prepared by introducing a protective group $M^1$ into the hydroxy group of a compound represented by the above general formula (XXIV) in the usual way.

Process 24

A compound represented by the above general formula (XXI) can be obtained by subjecting a compound represented by the above general formula (XXV) to 1) reduction using a reducing agent such as diisobutylaluminum hydride in an inert solvent, and then to 2) oxidation using an oxidizing agent such as a Dess-Martin reagent in an inert solvent. As the solvent used in the reduction, for example, tetrahydrofuran, dichloromethane, a mixed solvent thereof or the like can be illustrated, the reaction temperature is usually from −20° C. to reflux temperature, and the reaction time is usually from 1 hour to 1 day, varying based on a used starting material, solvent and reaction temperature. As the solvent used in the oxidation, for example, chloroform, dichloromethane or the like can be illustrated, the reaction temperature is usually from 0° C. to reflux temperature, and the reaction time is usually from 1 hour to 1 day, varying based on a used starting material, solvent and reaction temperature.

In the above production methods, a compound having a hydroxy group, a thiol group, an amino group and/or a carboxylic group can be subjected to the reaction after optionally introducing a protective group in the usual way as occasion demands. The protective group can be removed in the usual way in any subsequent process as occasion demands.

The compounds represented by the above general formula (I) of the present invention obtained by the above production processes can be isolated and purified by conventional separation means such as fractional recrystallization, purification using chromatography, solvent extraction and solid phase extraction.

The nitrogen-containing heterocyclic derivatives represented by the above general formula (I) of the present invention and prodrugs thereof can be converted into their pharmaceutically acceptable salts in the usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and addition salts with organic bases such as N-methyl-D-glucamin, N,N'-dibenzylethylenediamine, 2-aminoethanol, tris(hydroxymethyl)aminomethane, arginine, lysine and the like.

The compounds represented by the above general formula (I) of the present invention and salts thereof and prodrugs thereof include their solvates with pharmaceutically acceptable solvents such as ethanol and water.

Among the nitrogen-containing heterocyclic derivatives represented by the above general formula (I) of the present invention and prodrugs thereof, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

The nitrogen-containing heterocyclic derivatives represented by the above general formula (I) of the present invention and prodrugs thereof are able to show an activity of lowering blood glucose level by an excellent inhibitory activity in human SGLT2. Therefore, they are extremely useful as drugs for the prevention or treatment of a disease associated with hyperglycemia such as diabetes, diabetic complications (e.g., retinopathy, neuropathy, nephropathy, ulcer, macroangiopathy), obesity, hyperinsulinemia, glucose metabolism disorders, hyperlipidemia, hypercholesterolemia, hypertriglyceridemia, lipid metabolism disorders, a therosclerosis, hypertension, congestive heart failure, edema, hyperuricemia, gout or the like.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhydantoin, EGB-761, bimoclomol, sulodexide, Y-128, a hydroxymethylglutaryl coenzyme A reductase inhibitor, a fibric acid derivative, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of same or different administration route, and administration at different dosage intervals as separated preparations in way of same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of coadministrated drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorders, hyperlipidemia, hypercholesterolemia, hypertriglyceridemia, lipid metabolism disorders or atherosclerosis, and more preferably for diabetes, hyperinsulinemia or glucose metabolism disorders because of improving the disturbance of insulin signal transduction in peripheral tissues and enhancing glucose uptake into the tissues from the blood, leading to lowering blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorders, and more preferably for diabetes or glucose metabolism disorders because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorders, and more preferably for diabetes, hyperinsulinemia or glucose metabolism disorders because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilyl-urea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorders, and more preferably for diabetes or glucose metabolism disorders because of lowering blood glucose level by acting on pancreatic β-cells and enhancing the insulin secretion.

As insulin or insulin analogues, human insulin, animal-deprived insulin and human insulin analogues are illustrated. These agents are used preferably for diabetes, diabetic complications or glucose metabolism disorders, and more preferably for diabetes or glucose metabolism disorders.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, NN-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists; AZM-134, LY-315902 and the like are illustrated; and as amylin, amylin analogues or amylin agonists, pramlintide acetate and the like are illustrated. These drugs, glucose-6-phosphatase inhibitors, D-chiroinositol, glycogen synthase kinase-3 inhibitors, glucagon-like peptide-1 are used preferably for diabetes, diabetic complications, hyperinsulinemia or glucose metabolism disorders, and more preferably for diabetes or glucose metabolism disorders.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation end products formation inhibitors, pyridoxamine, OPB-9195, ALT-946, ALT-711, pimagedine hydrochloride and the like are illustrated. Advanced glycation end products formation inhibitors are preferably used for diabetic complications because of inhibiting formation of advanced glycation end products which are accelerated in continuous hyperglycemic condition in diabetes and declining cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcrit factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecarnine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methyl-hidantoin, EGB-761, bimoclomol, sulodexide and Y-128 are preferably used for diabetic complications.

As hydroxymethyl glutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethyl glutaryl coenzyme A reductase inhibitors are used preferably for hyperlipidemia, hypercholesterolemia, hypertriglyceridemia, lipid metabolism disorders or atherosclerosis, and more preferably for hyperlipidemia, hypercholesterolemia or atherosclerosis because of lowering blood cholesterol level by inhibiting hydroxymethyl glutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for hyperinsulinemia, hyperlipidemia, hypercholesterolemia, hypertriglyceridemia, lipid metabolism disorders or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696, YM178 and the like are illustrated. $\beta_3$-Adrenoceptor agonists are used preferably for obesity, hyperinsulinemia, hyperlipidemia, hypercholesterolemia, hypertriglyceridemia or lipid metabolism disorders, and more preferably for obesity or hyperinsulinemia because of stimulating $\beta_3$-adrenoceptor in adipose tissue and enhancing the fatty acid oxidation, leading to induction of energy expenditure.

As acyl-coenzyme A: cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A: cholesterol acyltransferase inhibitors are used preferably for hyperlipidemia, hyper-cholesterolemia, hypertriglyceridemia or lipid metabolism disorders, and more preferably for hyperlipidemia or hyper-cholesterolemia because of lowering blood cholesterol level by inhibiting acyl-coenzyme A: cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, orlistat, ATL-962, AZM-131, RED-103004 and the like are illustrated; as carnitine palmitoyltransferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorders.

As appetite suppressants, monoamine reuptake inhibitors, serotonin reuptake inhibitors, serotonin releasing stimulants, serotonin agonists (especially $5HT_{2C}$-agonists), noradrenalin reuptake inhibitors, noradrenalin releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine-and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotropin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone receptor antagonists, agouti-related protein inhibitors and orexin receptor antagonists are illustrated. Concretely, as monoamine reuptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as $H_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorders, hyperlipidemia, hypercholesterolemia, hypertriglyceridemia, lipid metabolism disorders, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-α, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of use in combination with drugs other than SGLT2 inhibitors, for example, for diabetes, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and insulin or an insulin analogue is most preferable. Similarly, for diabetic complications, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, for obesity, the combination with at least one member of the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinositol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment,various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting with and dissolving in an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a nitrogen-containing heterocyclic derivative represented by the above general formula (I) or a pharmaceutically acceptable salt thereof, or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased depending on the dosage of the drugs other than SGLT2 inhibitors.

EXAMPLES

The present invention is further illustrated in more detail by way of the following Examples and Test Examples. However, the present invention is not limited thereto.

Example 1

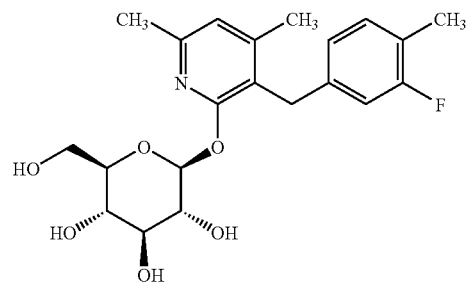

Process 1

2-Benzyloxy-4,6-dimethylpyridin-3-yl
3-fluoro-4-methyl-phenyl methanol

A Grignard reagent was prepared in the usual way using 1-bromo-3-fluoro-4-methylbenzene (0.53 g), Magnesium (0.069 g), a catalytic amount of iodine and tetrahydrofuran (5 mL). To a tetrahydrofuran solution of the Grignard reagent was added a solution of 2-benzyloxy-3-formyl-4,6-dimethylpyridene (0.34 g) in tetrahydrofuran (5 mL) at 0° C. After the reaction mixture was stirred at room temperature for 1 hour, a saturated aqueous ammonium solution and water were added, and the mixture was extracted with diethyl ether. The organic layer was washed with brine and dried over anhydrous magnesium sulfate, and the solvent was removed under reduced pressure. The residue was purified by column chromatography on silica gel (hexane/ethyl acetate=6/1) to give the title compound (0.39 g).

Process 2

3-(3-Fluoro-4-methylbenzyl)-4,6-dimethyl-1H-pyridin-2-one

To a solution of 2-benzyloxy-4,6-dimethylpyridin-3-yl 3-fluoro-4-methylphenyl methanol (0.39 g) in ethanol (10 mL) was added a catalytic amount of palladium carbon powder, and the mixture was stirred at room temperature under a hydrogen atmosphere overnight. After the insoluble material was removed by filtration, the solvent of the filtrate was removed to give the title compound (0.22 g).

$^1$H-NMR (CDCl$_3$) δ ppm: 2.14 (3H, s), 2.20 (3H, d, J=1.1 Hz), 2.22 (3H, s), 3.88 (2H, s), 5.86 (1H, s), 6.85-6.95 (2H, m), 6.95-7.10 (1H, m)

Process 3

2-(2,3,4,6-Tetra-O-acethyl-β-D-glucopyranosyloxy)-3-(3-fluoro-4-methylbenzyl)-4,6-dimethylpyridine To a solution of 3-(3-fluoro-4-methylbenzyl)-4,6-dimethyl-1H-pyridin-2-one (0.08 g) and acetobromo-α-D-glucose (0.15 g) in dichloromethane (2 mL) was added silver carbonate (0.090 g), and the mixture was stirred at room temperature overnight in the shade. The insoluble material was removed by filtration, and the filtrate was purified by column chromatography on aminopropylated silica gel (dichloromethane) to give the title compound (0.17 g).

$^1$H-NMR (CDCl$_3$) δ ppm: 1.78 (3H, s), 2.00 (3H, s), 2.04 (3H, s), 2.04 (3H, s), 2.16 (3H, s), 2.17-2.20 (3H, m), 2.38 (3H, s), 3.79 (1H, d, J=15.7 Hz), 3.93 (1H, ddd, J=2.5, 4.7, 10.1 Hz), 3.97 (1H, d, J=15.7 Hz), 4.13 (1H, dd, J=2.5; 12.3 Hz), 4.25 (1H, dd, J=4.7, 12.3 Hz), 5.10-5.20 (1H, m), 5.25-5.40 (2H, m), 6.15-6.25 (1H, m), 6.60-6.70 (2H, m), 6.75-6.80 (1H, m), 6.95-7.05 (1H, m)

Process 4

2-(β-D-Glucopyranosyloxy)-3-(3-fluoro-4-methylbenzyl)-4,6-dimethylpyridine

To a solution of 2-(2,3,4,6-tetra-O-acetyl-β-D-gluco-pyranosyloxy)-3-(3-fluoro-4-methylbenzyl)-4,6-dimethyl-pyridine (0.17 g) in methanol (5 mL) was added sodium methoxide (28% methanol solution, 0.028 mL), and the mixture was stirred at room temperature for 1 hour. The solvent of the reaction mixture was removed, and the residue was purified by column chromatography on silica gel (dichloromethane/methanol=10/1) to give the title compound (0.081 g).

$^1$H-NMR (CD$_3$OD) δ ppm: 2.17 (6H, s), 2.36 (3H, s), 3.30-3.55 (4H, m), 3.67 (1H, dd, J=5.3, 11.9 Hz), 3.84 (1H, dd, J=2.4, 11.9 Hz), 3.94 (1H, d, J=15.6 Hz), 4.06 (1H, d, J=15.6 Hz), 5.85-6.00 (1H, m), 6.70-6.80 (1H, m), 6.80-6.95 (2H, m), 7.00-7.10 (1H, m)

Examples 2-3

The compounds described in Table 1 were prepared in a similar manner to that described in Example 1 using corresponding starting materials.

TABLE 1

| Example number | Chemical structure | $^1$H-NMR (CD$_3$OD) δ ppm: |
|---|---|---|
| Example 2 | (structure: 3-(3-methylbenzyl)-pyridine β-D-glucopyranosyloxy derivative) | 2.29 (3H, s), 3.35-3.60 (4H, m), 3.68 (1H, dd, J=5.0. 12.0Hz), 3.84 (1H, d, J=12.0Hz), 3.92(1H, d, J=15.4Hz), 3.96 (1H, d, J=15.4Hz), 5.80-5.95 (1H, m), 6.85-7.20 (5H, m), 7.30-7.45 (1H, m), 7.90-8.05 (1H, m) |
| Example 3 | (structure: 3-(2-methylbenzyl)-pyridine β-D-glucopyranosyloxy derivative) | 2.20 (3H, s), 3.35-3.60 (4H, m), 3.70 (1H, dd, 5.0, 12.0Hz), 3.85 (1H, dd, J=2.1, 12.0Hz), 3.97 (1H, d, J=16.7Hz), 4.02 (1H, d, J=16.7Hz), 5.85-5.95 (1H, m), 6.80-6.95 (1H, m), 7.00-7.25 (5H, m), 7.90-8.05 (1H, m) |

Test Example 1

Assay for Inhibitory Effects on Human SGLT2 Activity

1) Cloning and Construction of the Vector Expressing Human SGLT2

The cDNA library was prepared for PCR amplification by reverse transcription from total RNA deprived from human kidney (Ori gene) using oligo-dT as a primer. Using this cDNA library as a template, the base sequence coding 2 to 2039 bp of human SGLT2 (ACCESSION: M95549, M95299), which was reported by R. G. Wells et al., was amplified by PCR method and inserted into the multi-cloning site of pcDNA3.1(−) (Invitrogen). The DNA sequence inserted was perfectly matched to the previously reported sequence.

2) Establishment of Cell Line Stably Expressing Human SGLT2

The expression vector of human SGLT2 was digested by Sca I into a linear DNA. The linear DNA was transfected into CHO-K1 cells by means of lipofection (Effectene Transfection Reagent: QIAGEN). Neomycin resistant cell lines were obtained by culture in the medium containing 1 mg/mL of G418 (LIFE TECHNOLOGIES), and then the activity against the uptake of methyl-α-D-gluco-pyranoside was measured by the method described below. The cell line, which showed the greatest uptake activity, was selected and designated as CS2-5E. Afterward, CS2-5E cells were cultured in the presence of G418 at 200 μg/mL.

3) Measurement of the Inhibitory Activity Against the Uptake of methyl-α-D-glucopyranoside (α-MG)

CS2-5E cells were seeded into a 96-well culture plate at a density of 3×10⁴ cells/well and cultured for 2 days, and were used in the uptake assay. A mixture of non-radiolabeled (Sigma) and $^{14}$C-labeled α-MG (Amersham Pharmcia Biotec) was added to the uptake buffer (pH 7.4; containing 140 mM sodium chloride, 2 mM potassium chloride, 1 mM calcium chloride, 1 mM magnesium chloride, 10 mM 2-[4-(2-hydroxyethyl)-1-piperazinyl]ethane sulfonic acid, and 5 mM tris (hydroxymethyl)aminomethane) at the final concentration of 1 mM. A test compound was dissolved in dimethyl sulfoxide, and then appropriately diluted with distilled water. The test compound solution was added to the uptake buffer containing 1 mM α-MG, and designated as a measurement buffer. For the control group, the measurement buffer without any test compound was prepared. For measuring the basal uptake, a basal uptake measurement buffer which contains 140 mM chorine chloride instead of sodium chloride was prepared. After removing the culture medium of cells, 180 μL of the pre-treatment buffer (the basal uptake buffer without α-MG) was added to each well and incubated at 37° C. for 10 minutes. After repeating once the same treatment, the pre-treatment buffer was removed. To each well was added 75 μL of the measurement buffer or the basal uptake buffer was added and incubated at 37° C. After 1 hour, the measurement buffer was removed, and cells were washed twice with 180 μL per well of the washing buffer (the basal uptake buffer containing 10 mM non-labeled α-MG). The cells were solubilized by 75 μL per well of 0.2 mol/L sodium hydroxide. The cell lysates were transferred into PicoPlates (Packard), and then added 150 μL of MicroScint-40 (Packard) and mixed. Radioactivity was measured by means of scintillation counter (Packard). One hundred % was set to the difference between the uptake in the control group and the basal uptake, and the percentage of the uptake of methyl α-D-glucopyranoside at each drug concentration were calculated. The drug concentration, at which 50% uptake of methyl α-D-glucopyranoside was inhibited (IC$_{50}$ value), was calculated using logit plot. The results were shown in Table 2.

TABLE 2

| Test compound | IC$_{50}$ (nM) |
|---|---|
| Example 1 | 3 |

INDUSTRIAL APPLICABILITY

The nitrogen-containing heterocyclic derivatives represented by the above general formula (I) of the present invention, pharmaceutically acceptable salts thereof and prodrugs thereof show an excellent hypoglycemic effect by excreting excess glucose into the urine through preventing the reabsorption of glucose at the kidney because they exhibit an excellent inhibitory activity in human SGLT2. The present invention can provide drugs for the prevention or treatment of a disease associated with hyperglycemia such as diabetes, diabetic complications, obesity or the like.

The invention claimed is:

1. A nitrogen-containing heterocyclic derivative represented by the general formula:

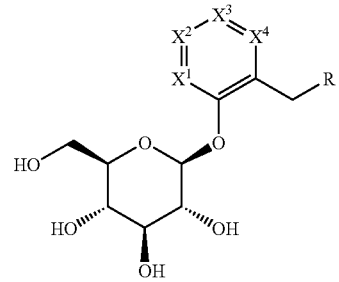

wherein
$X^1$ represents N or $CR^1$;
$X^2$ represents N or $CR^2$;
$X^3$ represents N or $CR^3$;
$X^4$ represents N or $CR^4$;
and with the proviso that one or two of $X^1$, $X^2$, $X^3$ and $X^4$ represent N;
R represents a $C_{3-8}$ cycloalkyl group which may have the same or different 1 to 3 groups selected from the following substituent group (A), a $C_{6-10}$ aryl group which may have the same or different 1 to 3 groups selected from the following substituent group (B), a $C_{2-9}$ heterocycloalkyl group which may have the same or different 1 to 3 groups selected from the following substituent group (A), or a $C_{1-9}$ heteroaryl group which may have the same or different 1 to 3 groups selected from the following substituent group (B);
$R^1$ to $R^4$ are the same or different, independently represents a hydrogen atom or a group selected from the following substituent group (D);
substituent group (A) consists of a halogen atom, a nitro group, a cyano group, an oxo group, -$G^1$, -$OG^2$, -$SG^2$, —N($G^2$)$_2$, —C(=O)$G^2$, —C(=O)$OG^2$—C(=O)N($G^2$)$_2$, —S(=O)$_2G^2$, —S(=O)$_2OG^2$, —S(=O)$_2$N($G^2$)$_2$, —S(=O)$G^1$, —OC(=O)$G^1$, —OC(=O)N($G^2$)$_2$, —NHC(=O)$G^2$, —OS(=O)$_2G^1$, —NHS(=O)$_2G^1$ and —C(=O)NHS(=O)$_2G^1$;
substituent group(B) consists of a halogen atom, a nitro group, a cyano group, -$G^1$, —$OG^2$, —$SG^2$, —N($G^2$)$_2$, -$G^3OG^4$, -$G^3N(G^4)_2$, -C(=O)$G^2$, -C(=O)$OG^2$, -C(=O)N($G^2$)$_2$, —S(=O)$_2G^2$, —S(=O)$_2OG^2$, —S(=O)$_2$N($G^2$)$_2$, —S(=O)$G^1$, —OC(=O)$G^1$, —OC(=O)N($G^2$)$_2$, —NHC(=O)$G^2$, —OS(=O)$_2G^1$, —NHS(=O)$_2G^1$ and —C(=O)NHS(=O)$_2G^1$
in the substituent group (A) and/or (B), $G^1$ represents a $C_{1-6}$ alkyl group which may have the same or different 1 to 3 groups selected from the following substituent group (C), a $C_{2-6}$ alkenyl group which may have the same or different 1 to 3 groups selected from the following substituent group (C), a $C_{2-6}$ alkynyl group which may have the same or different 1 to 3 groups selected from the following substituent group (C), a $C_{3-8}$ cycloalkyl group which may have the same or different 1 to 3 groups selected from the following substituent group (C), a $C_{6-10}$ aryl group which may have the same or different 1 to 3 groups selected from the following substituent group (D), a $C_{2-9}$ heterocycloalkyl group which may have the same or different 1 to 3 groups selected from the following substituent group (C), a $C_{1-9}$ heteroaryl group which may have the same or different 1 to 3 groups selected from the following substituent group (D);

G² represents a hydrogen atom, a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (D), a C₁₋₉ heteroaryl group which may have the same or different 1 to 3 groups selected from the following substituent group (D), and with the proviso that G² are the same or different when there are more than one G² in the substituents;

G³ represents a C₁₋₆ alkyl group;

G⁴ represents a C₁₋₆ alkyl group which may have the same or different 1 to 3 groups selected from the following substituent group (C), and with the proviso that G⁴ are the same or different when there are more than one G⁴ in the substituents;

substituent group (C) consists of a halogen atom, a nitro group, a cyano group, an oxo group, -G⁵, —OG⁶, —SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC(=O)N(G⁶)₂, —NHC(=O)G⁶, —OS(=O)₂G⁵, —NHS(=O)₂G⁵ and —C(=O)NHS(=O)₂G⁵;

substituent group (D) consists of a halogen atom, a nitro group, a cyano group, -G⁵, —OG⁶, -SG⁶, —N(G⁶)₂, —C(=O)G⁶, —C(=O)OG⁶, —C(=O)N(G⁶)₂, —S(=O)₂G⁶, —S(=O)₂OG⁶, —S(=O)₂N(G⁶)₂, —S(=O)G⁵, —OC(=O)G⁵, —OC(=O)N(G⁶)₂, —NHC(=O)G⁶, —OS(=O)₂G⁵, —NHS(=O)₂G⁵ and —C(=O)NHS(=O)₂G⁵ in the substituent group (C) and/or (D), G⁵ represents a C₁₋₆ alkyl group, a HO—C₁₋₆ alkyl group, a C₂₋₆ alkenyl group, a C₂₋₆ alkynyl group, a C₃₋₈ cycloalkyl group, a C₆₋₁₀ aryl group, a C₂₋₉ heterocycloalkyl group or a C₁₋₉ heteroaryl group;

G⁶ represents a hydrogen atom, a C₁₋₆ alkyl group, a C₂₋₆ alkenyl group, a C₂₋₆ alkynyl group, a C₃₋₈ cycloalkyl group, a C₆₋₁₀ aryl group, a C₂₋₉ heterocycloalkyl group or a C₁₋₉ heteroaryl group, and with the proviso that G⁶ are the same or different when there are more than one G⁶ in the substituents and with the proviso that when X¹ and X³ independently represent N or CH;

X² represents N or CR², wherein R² represents a hydrogen atom, a halogen atom, a C₁₋₆ alkyl group, a C₃₋₈ cycloalkyl group, —O—C₁₋₆ alkyl, an amino group, —NH—C₂₋₇ acyl, —NH—C₁₋₆ alkyl or —N(C₁₋₆ alkyl)₂; and when X⁴ represents N or CR⁴, wherein R⁴ represents a hydrogen atom or a C₁₋₆ alkyl group, R represents the above-defined group except for the following substituent:

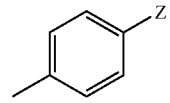

wherein Z represents a hydrogen atom, a halogen atom, a C₁₋₆ alkyl group which may have a substituent selected from the following substituent group (α), —O—C₁₋₆ alkyl which may have a substituent selected from the following substituent group (β), —S—C₁₋₆ alkyl which may have a substituent selected from the following substituent group (β) or a C₃₋₈ cycloalkyl group;

substituent group (α) consists of a halogen atom, a hydroxy group and —O—C₁₋₆ alkyl; and substituent group (β) consists of a hydroxy group and —O—C₁₋₆ alkyl, or a pharmaceutically acceptable salt thereof, or a prodrug thereof.

2. A nitrogen-containing heterocyclic derivative as claimed in claim 1 wherein R represents a phenyl group which may have the same or different 1 to 3 groups selected from the following substituent group (B), or a pharmaceutically acceptable salt thereof, or a prodrug thereof substituent group (B) consists of a halogen atom, a nitro group, a cyano group, -G¹, —OG², —SG², —N(G²)₂, -G³OG⁴, -G³N(G⁴)₂, —C(=O)G², —C(=O)OG², —C(=O)N(G²)₂, —S(=O)₂G², —S(=O)₂OG², —S(=O)₂N(G²)₂, —S(=O)G¹, —OC(=O)G¹, —OC(=O)N(G²)₂, —NHC(=O)G², —OS(=O)₂G¹, —NHS(=O)₂G¹ and —C(=O)NHS(=O)₂G¹ in the substituent group (B), G¹ represents a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group (C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (C), a C₁₋₉ heteroaryl group which may have the same or different 1 to 3 groups selected from the following substituent group (D);

G² represents a hydrogen atom, a C₁₋₆ alkyl group which may have the same or different 1 to 3 groups selected from the following substituent group (C), a C₂₋₆ alkenyl group which may have the same or different 1 to 3 groups selected from the following substituent group (C), a C₂₋₆ alkynyl group which may have the same or different 1 to 3 groups selected from the following substituent group(C), a C₃₋₈ cycloalkyl group which may have the same or different 1 to 3 groups selected from the following substituent group (C), a C₆₋₁₀ aryl group which may have the same or different 1 to 3 groups selected from the following substituent group (D), a C₂₋₉ heterocycloalkyl group which may have the same or different 1 to 3 groups selected from the following substituent group (D), a C₁₋₉ heterooalkyl group which may have the same or different 1 to 3 groups selected from the following substituent group (D), and with the proviso that $G^2$ are the same or different when there are more than one $G^2$ in the substituents;

$G^3$ represents a $C_{1-6}$ alkyl group;

$G^4$ represents a $C_{1-6}$ alkyl group which may have the same or different 1 to 3 groups selected from the following substituent group (C), and with the proviso that $G^4$ are the same or different when there are more than one $G^4$ in the substituents;

substituent group (C) consists of a halogen atom, a nitro group, a cyano group, an oxo group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$; and substituent group (D) consists of a halogen atom, a nitro group, a cyano group, $-G^5$, $-OG^6$, $-SG^6$, $-N(G^6)_2$, $-C(=O)G^6$, $-C(=O)OG^6$, $-C(=O)N(G^6)_2$, $-S(=O)_2G^6$, $-S(=O)_2OG^6$, $-S(=O)_2N(G^6)_2$, $-S(=O)G^5$, $-OC(=O)G^5$, $-OC(=O)N(G^6)_2$, $-NHC(=O)G^6$, $-OS(=O)_2G^5$, $-NHS(=O)_2G^5$ and $-C(=O)NHS(=O)_2G^5$ in the substituent group (C) and/or (D), $G^5$ represents a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{2-9}$ heterocycloalkyl group or a $C_{1-9}$ heteroaryl group; and $G^6$ represents a hydrogen atom, a $C_{1-6}$ alkyl group, a $C_{2-6}$ alkenyl group, a $C_{2-6}$ alkynyl group, a $C_{3-8}$ cycloalkyl group, a $C_{6-10}$ aryl group, a $C_{2-9}$ heterocycloalkyl group or a $C_{1-9}$ heteroaryl group, and with the proviso that $G^6$ are the same or different when there are more than one $G^6$ in the substituents.

3. A pharmaceutical composition comprising as an active ingredient a nitrogen-containing heterocyclic derivative as claimed in claim 1 or 2, or a pharmaceutically acceptable salt thereof, or a prodrug thereof.

4. A pharmaceutical composition as claimed in claim 3 wherein the composition is a human SGLT2 inhibitor.

5. A method for the treatment of a disease associated with hyperglycemia, which comprises administering an effective amount of a nitrogen-containing heterocyclic derivative as claimed in claim 1 or 2, or a pharmaceutically acceptable salt thereof, or a prodrug thereof.

6. A pharmaceutical combination which comprises (A) a nitrogen-containing heterocyclic derivative as claimed in claim 1 or 2, or a pharmaceutically acceptable salt thereof, or a prodrug thereof, and (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a β$_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α$_2$-adrenoceptor agonist, an antiplatelets agent, a uric acid synthesis inhibitor, a uricosuric agent and a urinary alkalinizer.

7. A pharmaceutical combination as claimed in claim 6 for the treatment of a disease associated with hyperglycemia.

8. A pharmaceutical combination as claimed in claim 7 wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant, and the disease associated with hyperglycemia is diabetes.

9. A pharmaceutical combination as claimed in claim 8 wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist.

10. A pharmaceutical combination as claimed in claim 9 wherein a component (B) is at least one member selected from the group consisting of an insulin sensitivity enhancer, a glucose absorption inhibitor, a biguanide, an insulin secretion enhancer and insulin or an insulin analogue.

11. A pharmaceutical combination as claimed in claim 7 wherein a component (B) is at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhydantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent, and the disease associated with hyperglycemia is diabetic complications.

12. A pharmaceutical combination as claimed in claim 11 wherein a component (B) is at least one member selected from the group consisting of an aldose reductase inhibitor, an angiotensin-converting enzyme inhibitor, a neutral endopeptidase inhibitor and an angiotensin II receptor antagonist.

13. A pharmaceutical combination as claimed in claim 7 wherein a component (B) is at least one member selected from the group consisting of an insulin sensitivity enhancer, a glucose absorption inhibitor, a biguanide, an insulin secretion enhancer, an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $β_3$-adrenoceptor agonist and an appetite suppressant, and the disease associated with hyperglycemia is obesity.

14. A pharmaceutical combination as claimed in claim 13 wherein a component (B) is at least one member selected from the group consisting of a $β_3$-adrenoceptor agonist and an appetite suppressant.

15. A pharmaceutical combination as claimed in claim 14 wherein the appetite suppressant is a drug selected from the group consisting of a monoamine reuptake inhibitor, a serotonin reuptake inhibitor, a serotonin releasing stimulant, a serotonin agonist, a noradrenaline reuptake inhibitor, a noradrenaline releasing stimulant, an $α_1$-adrenoceptor agonist, a $β_2$-adrenoceptor agonist, a dopamine agonist, a cannabinoid receptor antagonist, a γ-aminobutyric acid receptor antagonist, a $H_3$-histamine antagonist, L-histidine, leptin, a leptin analogue, a leptin receptor agonist, a melanocortin receptor agonist, α-melanocyte stimulating hormone, cocaine-and amphetamine-regulated transcript, mahogany protein, an enterostatin agonist, calcitonin, calcitonin-gene-related peptide, bombesin, a cholecystokinin agonist, corticotropin-releasing hormone, a corticotropin-releasing hormone analogue, a corticotropin-releasing hormone agonist, urocortin, somatostatin, a somatostatin analogue, a somatostatin receptor agonist, pituitary adenylate cyclase-activating peptide, brain-derived neurotrophic factor, ciliary neurotrophic factor, thyrotropin-releasing hormone, neurotensin, sauvagine, a neuropeptide Y antagonist, an opioid peptide antagonist, a galanin antagonist, a melanin-concentrating hormone receptor antagonist, an agouti-related protein inhibitor and an orexin receptor antagonist.

16. A method for the treatment of a disease associated with hyperglycemia, which comprises administering an effective amount of (A) a nitrogen-containing heterocyclic derivative as claimed in claim 1 or 2, or a pharmaceutically acceptable salt thereof, or a prodrug thereof, in combination with (B) at least one member selected from the group consisting of an insulin sensitivity enhancer, a glucose absorption inhibitor, a biguanide, an insulin secretion enhancer, insulin or an insulin analogue, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation end products formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhydantoin, EGB-761, bimoclomol, sulodexide, Y-128, a hydroxymethyl-glutaryl coenzyme A reductase inhibitor, a fibric acid derivative, a $β_3$-adrenoceptor agonist, an acyl-coenzyme A: cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

17. A method for the treatment as claimed in claim 5, wherein the disease associated with hyperglycemia is diabetes.

18. A method for the treatment as claimed in claim 5, wherein the disease associated with hyperglycemia is diabetic complications.

19. A method for the treatment as claimed in claim 5, wherein the disease associated with hyperglycemia is obesity.

20. A method for inhibiting a human SGLT2, which comprises administering an effective amount of a nitrogen-containing heterocyclic derivative as claimed in claim 1, or a pharmaceutically acceptable salt thereof, or a prodrug thereof.

21. A method for inhibiting a human SGLT2, which comprises administering an effective amount of a nitrogen-containing heterocyclic derivative as claimed in claim 2, or a pharmaceutically acceptable salt thereof, or a prodrug thereof.

* * * * *

UNITED STATES PATENT AND TRADEMARK OFFICE
CERTIFICATE OF CORRECTION

PATENT NO. : 7,655,633 B2
APPLICATION NO. : 10/540519
DATED : February 2, 2010
INVENTOR(S) : Hideki Fujikura et al.

It is certified that error appears in the above-identified patent and that said Letters Patent is hereby corrected as shown below:

In claim 2 at column 38, line 65:

Delete "$C_{1-9}$ heterooalkyl" and insert --$C_{1-9}$ heteroaryl--

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,655,633 B2 |
| APPLICATION NO. | : 10/540519 |
| DATED | : February 2, 2010 |
| INVENTOR(S) | : Fujikura et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 992 days.

Signed and Sealed this

Twenty-third Day of November, 2010

David J. Kappos
*Director of the United States Patent and Trademark Office*